United States Patent [19]

Jackson

[11] Patent Number: 4,801,293
[45] Date of Patent: Jan. 31, 1989

[54] APPARATUS AND METHOD FOR DETECTING PROBE PENETRATION OF HUMAN EPIDURAL SPACE AND INJECTING A THERAPEUTIC SUBSTANCE THEREINTO

[76] Inventor: Anthony Jackson, 13 Cayuse Lane Rancho, Palos Verdes, Calif. 90274

[21] Appl. No.: 134,699

[22] Filed: Dec. 18, 1987

Related U.S. Application Data

[63] Continuation-in-part of Ser. No. 930,211, Nov. 13, 1986, abandoned, which is a continuation of Ser. No. 785,923, Oct. 9, 1985, Pat. No. 4,623,335.

[51] Int. Cl.[4] .............................................. A61M 5/00
[52] U.S. Cl. ...................................... 604/51; 604/117; 604/118
[58] Field of Search .......................... 604/51, 118, 117; 128/673–675, 748

[56] References Cited

U.S. PATENT DOCUMENTS

| | | | |
|---|---|---|---|
| 2,866,453 | 12/1958 | Jewitt | 128/674 |
| 3,062,202 | 11/1962 | Ayman et al. | 128/674 |
| 3,183,722 | 5/1965 | Unger et al. | 128/673 |
| 3,581,733 | 6/1971 | Grandjean | 128/673 |
| 3,610,228 | 10/1971 | Temkin | 128/673 |
| 3,720,201 | 3/1973 | Ramsey, III | 128/673 |
| 3,730,168 | 5/1973 | McWhorter | 128/748 |
| 3,807,389 | 4/1974 | Miller et al. | 128/674 |
| 3,863,506 | 2/1975 | Borsanyi | 128/673 X |
| 3,920,002 | 11/1975 | Oye et al. | 604/118 X |
| 3,934,576 | 1/1976 | Danielsson | 604/118 X |
| 4,192,319 | 3/1980 | Hargens et al. | 128/673 X |
| 4,217,911 | 8/1980 | Layton | 604/118 X |
| 4,252,126 | 2/1981 | Manol | 128/673 |
| 4,300,572 | 11/1981 | Knighton | 128/673 X |
| 4,535,773 | 8/1985 | Yoon | 604/118 X |

*Primary Examiner*—Stephen C. Pellegrino

[57] ABSTRACT

A method for detecting probe penetration of human (i) target tissue having predetermined internal pressure and (ii) epidural space having essentially negative gauge pressure relative to atmosphere pressure and enlarging the epidural space in the neighborhood of said probe which includes inserting a hollow probe into the human body towards the internal target tissue and gradually increasing pressure in a closed volume defined by the probe interior and a conduit communicating therewith until a moveable piston slideably resident within the conduit and having a passageway therethrough connecting the portion of the conduit interior communicating with the hollow probe with an orifice in a laterial surface of the moveable piston slideably contacting said conduit interior, moving in response to pressure within the conduit opposing predetermined bias force applied to the moveable piston, reaches a predetermined position, at which the lateral surface orifice of the moveable piston communicates with ambient air via a passageway through the wall of the conduit, corresponding to pressure in the closed volume equaling the predetermined internal pressure.

Apparatus for detecting probe penetration of human (i) target tissue having predetermined internal pressure and (ii) epidural space and for enlarging said epidural space away from said probe which includes: an elongated hollow probe, a valve having first and second orifices with the first orifice communicating with the hollow probe, a conduit communicating with the second orifice of the valve, a piston movable resident within the conduit in response to conduit pressure, for limiting pressure within the conduit to the predetermined internal pressure and providing visible indication upon pressure within the conduit reaching the predetermined internal pressure and has a hand squeezable bulb communicating with the conduit intermediate the movable piston and the valve, for increasing pressure within the conduit and the probe until the movable piston limits pressure within the conduit to the predetermined pressure.

5 Claims, 1 Drawing Sheet

U.S. Patent  Jan. 31, 1989  4,801,293
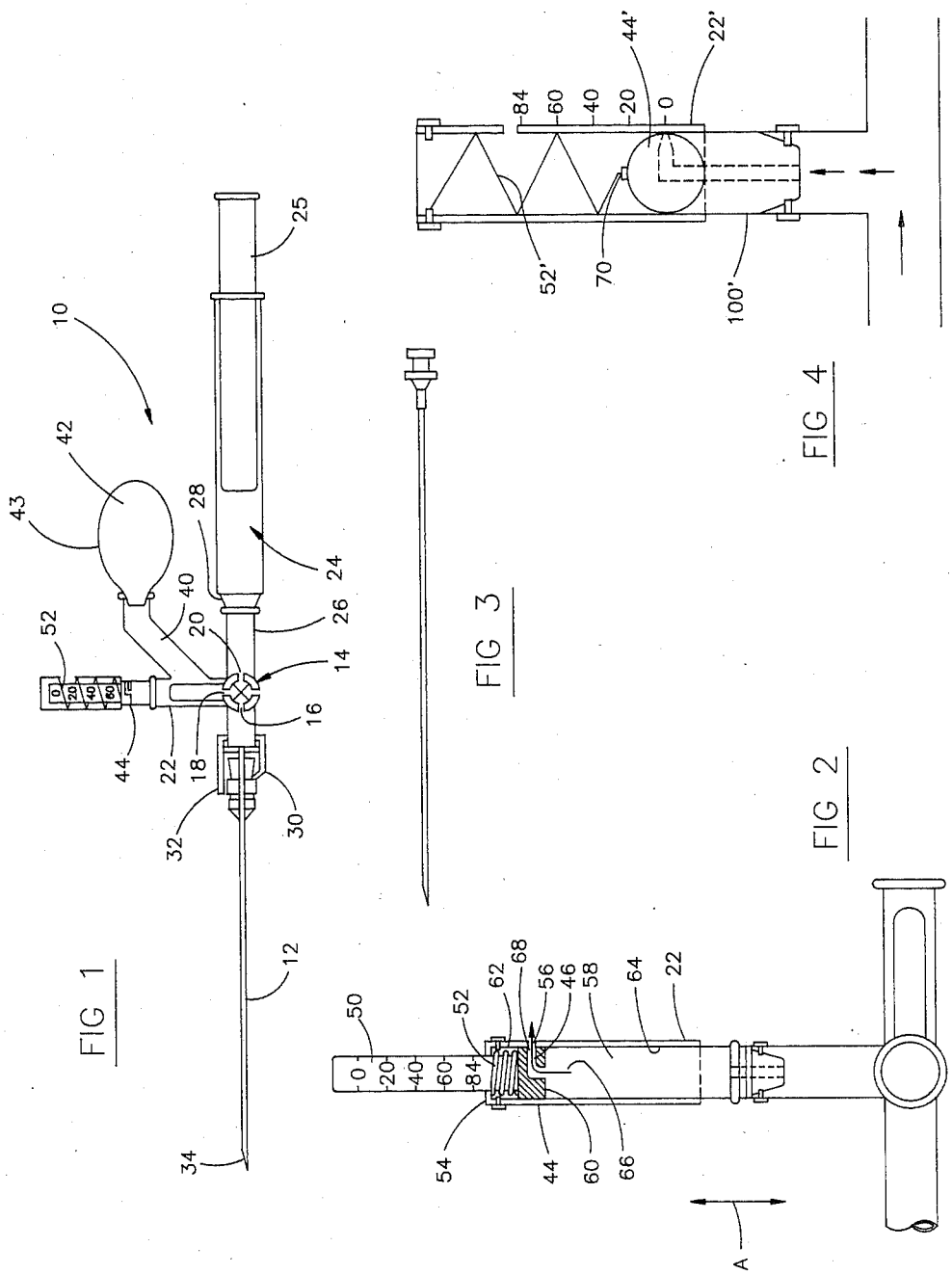

APPARATUS AND METHOD FOR DETECTING PROBE PENETRATION OF HUMAN EPIDURAL SPACE AND INJECTING A THERAPEUTIC SUBSTANCE THEREINTO

This application is a continuation-in-part of co-pending patent application Ser. No. 930,211, filed on Nov. 13, 1986 now abandoned, which is a continuation of patent application Ser. No. 785,923 filed Oct. 9, 1985, now issued U.S. Pat. No. 4,623,335.

FIELD OF THE INVENTION

This invention relates to methods and apparatus for detecting probe penetration of human internal target tissue having a predetermined internal pressure and to introduction of therapeutic substances close to or into the target tissue.

This invention further relates to apparatus and methods for detecting probe penetration of human epidural space having predetermined, essentially negative, gauge pressure and for enlarging the epidural space in the neighborhood of the probe tip by anteriorly displacing tissue bounding the epidural space away from the probe tip preparatory to injecting a therapeutically desired substance into the epidural space via the probe tip.

BACKGROUND OF THE INVENTION

In the human body the epidural space is a narrow but important anatomical space or void located in and traversing most of the length of the spine. The epidural space exhibits an internal pressure which research has determined to be at or below atmospheric pressure, customarily measured in units of centimeters of water. The epidural space is important because it may be used as a vehicle to introduce certain pharmaceutical agents at various positions along the spine. By introduction of anesthetics and/or medication into the epidural space at an appropriate position, a variety of pain causing maladies that afflict the body from head to toe may be treated. Also, the epidural space may be used for injection of anesthetics to provide regional anesthesia required for various types of surgery. This is especially important when general anesthesia may not be indicated due to a patient's condition or the particular surgery to be performed.

The epidural space is exceedingly narrow and close to the spinal cord; accordingly: accurate identification of the epidural space is quite important. Unfortunately, because of the small size of the epidural space, it is often difficult to locate, for even the most skilled physician.

One benchmark for locating the epidural space is the ligamentum-flavum. The ligamentum-flavum is a ligament having unique pressure characteristics which distinguish it from all other anatomical structures in the posterior spine. The ligamentum-flavum is useful in identifying and locating the epidural space because once the ligamentum-flavum is identified, the epidural space is easily identified—the epidural space lies only a few fractions of a centimeter anterior to the ligamentum-flavum.

As is well-known according to various anatomy handbooks, such as *Gray's Anatomy*, the spine has four major divisions—cervical, thoracic, lumbar and sacral. When probing the posterior back at a level below a spinous process, which process serves for attachment of muscles and ligaments, the major anatomical structures encountered when proceeding from dorsal to ventral are the skin, the supraspinous ligament, the interspinous ligament, the ligamentum-flavum, the epidural space, the dura, the sub-arachnoid space containing spinal fluid and, finally, the spinal cord.

The main body of the spinal cord ends at about the beginning of the lumbar portion of the spine, around the vertabrae generally identified $L_1$-$L_2$. Below this point the spinal cord divides into numerous small filaments, known as the tail of the horse or cauda-equina. The majority of epidural injections are performed below lumbar vertabrae $L_2$, to avoid the devastating consequences of an accidental spinal cord penetration. Because of this danger, many physicians and other clinicians shy away from performing upper level or cervical-thoracic epidural injections because confirmation of correct placement of the injecting needle in the epidural space is difficult, if not impossible, using apparatus and methods known heretofore.

The ligamentum-flavum consists of very dense fiberous-membranous tissue, in contrast to the more spongia-type of tissue prevalent in other posterior spinal structures. Because of its unique composition and characteristics, the ligamentum-flavum (which may be the "benchmark" referred to hereinafter) is the only anatomical area in the posterior spine which resists positive pressure directly applied in or to the it, using apparatus which is essentially exterior to the body. In other words, air or fluid may be applied in or to the ligamentum-flavum under positive pressure, whereupon diffusion of the air or gas through the ligamentum-flavum is resisted by this ligament, which does not readily transmit, permit diffusion of or propagate such air or gas pressure, in normal, healthy adult patients. In some patients the ligamentum-flavum is denser than in others. In patients with a less dense ligamentum-flavum, particularly in elderly people in which the integrity of the ligamentum-flavum tissue may have degraded, the ligamentum-flavum may permit slight diffusion of air or gas applied thereagainst. The ligamentum-flavum makes up the bulk of the posterior border of the epidural space.

DESCRIPTION OF THE PRIOR ART

Prior art known to applicant includes U.S. Pat. Nos. 2,396,351; 2,866,453; 3,062,202; 3,183,722; 3,610,228: 3,720,201: 3,730,168; 3,807,389: 4,162,673; 4,175,567; 4,186,750; 4,192,319: 4,215,699: 4,217,911 and 4,252,126; and D. C. Moore's *Regional Block*, 4th Edition (C. P. Thomas 1981). Of these U.S. Pat. Nos. 2,396,351, 2,866,453, 3,813,722, 4,162,673, 4,175,567, 4,186,750, 4,215,699 and *Regional Block* are believed to be the most relevant with respect to the invention disclosed and claimed herein.

U.S. Pat. No. 2,396,351 discloses a device for measuring pressure of spinal fluid wherein samples of spinal fluid may be withdrawn to determine spinal fluid pressure without concomitant danger of large spinal fluid loss (col. 1, lines 50 to 53) and without need to displace a large quantity of spinal fluid to obtain a reading on the pressure indicating device. Instead of attaching the device directly to a pressure indicating device to read pressure of the spinal fluid sample directly, pressure of the spinal fluid sample is read indirectly, using a diaphragm to divide a chamber into two chambers. One chamber (anterior to the diaphragm) is smaller than the posterior chamber. The anterior chamber receives a small sample of spinal fluid thereby displacing the diaphragm. The posterior chamber is adapted for connection to a device by which any desired fluid pressure can be created within the posterior chamber. Furthermore, the posterior chamber communicates with a pressure indicating device. Because the diaphragm is present, the pressure between the anterior and posterior chamber can be equalized and the pressure indicating device indicates indirectly the pressure of the spinal fluid sample in the anterior chamber by the corresponding amount of pressure needed in the posterior chamber to restore the displaced diaphragm to its original position.

U.S. Pat. No. 2,866,453 discloses a hypodermic syringe combined with a standard three-way stop cock communicating with a pressure sensitive diaphragm attached to a calibrated manometer. Upon harvesting a particular body fluid, such as blood or acetic fluid, with the hypodermic syringe, the fluid may be isolated by the stop cock in the diaphragm-manometer portion of the device, whereupon pressure measurements may be made and recorded.

U.S. Pat. No. 3,183,722 includes a transparent cylinder having pressure scale markings in centimeters or inches of either water or mercury, in which a spring and a gas-tight movable rod-piston assembly are provided. A hypodermic needle is used via which body fluids are shunted first through a transparent channeled nozzle and then into a transparent cylinder. Compression of air in the cylinder is achieved by manually downwardly displacing the piston rod until pressure of liquid exiting the body equals pressure of air being compressed by the piston within the cylinder. Once equilibrium is attained, pressure is read directly on the scale, using the piston position as the pressure indicator. The spring plays no active role in compression, serving only to return the piston back to its initial position once a measurement has been taken.

U.S. Pat. No. 4,162,673 discloses a method of testing a needle assembly positioned in the epidural space. The U.S. Pat. No. 4,162,673 method employs a needle assembly and an elongated passageway communicating between the needle tip and a shallow open cavity. The device allows a user to determine position of the assembly tip vis-a-vis the epidural space by determining whether liquid passes from the dish-shaped cavity into the passageway or into the exterior of the needle assembly. The basis for the foregoing is that the epidural space is characterized by negative pressure whereas the subarachnoid space is characterized by positive pressure. Thus, depending on the pressure differential, test liquid placed in the dish cavity of the needle assembly will either enter the passageway if the tip is located in the epidural space, or the test liquid will pass to the exterior of the needle assembly if the tip is located in the subarachnoid space. This method appears to operate on the principle underlying the hanging drop technique which is discussed below in connection with the Moore publication.

U.S. Pat. No. 4,175,567 discloses a method for locating the epidural space. The U.S. Pat. No. 4,175,567 patent is analogous to U.S. Pat. No. 4,162,673 with the exception that a dish-shaped cavity and test liquid are used to determine the location of the needle assembly. U.S. Pat. No. 4,175,567 uses a needle assembly having a flexible film defining a closed cavity communicating with a needle of the assembly. The U.S. Pat. No. 4,175,567 method comprises the steps of positioning a tip of the assembly adjacent the epidural space and advancing the assembly into the body. As the assembly advances, the film flexes inwardly when the needle assembly tip is in the epidural space of the patient's body because the epidural space is characterized by a negative pressure. If the assembly enters the subarachnoid space then the film flexes outwardly because the subarachnoid space is characterized by a positive pressure.

U.S. Pat. No. 4,186,750 discloses a position testing device as opposed to a method of locating the epidural space. The U.S. Pat. No. 4,186,750 device also comprises the dish-shaped cavity.

U.S. Pat. No. 4,215,699 discloses a position indicating device. This device is analogous to the U.S. Pat. No. 4,175,567 method which utilized the movement of a flexible film as a method of locating the epidural space.

Of further interest is the Moore publication. Pertinent parts of this reference disclose two techniques used by anesthesiologists to locate the epidural space. One technique illustrated in FIG. 273 on page 414 is the hanging-drop technique. The anesthiologist inserts a needle into the ligamentium-flavum or the interspinous ligament. The hub of the needle contains a drop of liquid. As the needle tip pierces the ligamentum-flavum and enters the epidural space, the drop of liquid is pulled into the needle because there is a pressure differential—the epidural space is characterized by a negative pressure and the ligamentum-flavum is characterized by positive pressure. Thus, when the tip of the needle enters the negative pressure epidural space, the drop of liquid is pulled into the needle as the pressure differential equalizes.

The Moore reference teaches that another technique used to locate the epidural space is the loss of resistance technique. The technique utilizes a pressure method. When the tip of the needle lies in the ligamentum-flavum it is very difficult to inject any liquid into the ligament. The needle is advanced slowly, while constant, unremitting thumb pressure is kept on the plunger of the syringe. Once the needle tip enters the epidural space, the contents of the syringe are rapidly discharged if constant, unremitting thumb pressure is exerted on the plunger. Furthermore, the Moore reference discloses that the apparent negative pressure results from the needle pushing the epidural space and dura forward.

While these references illustrate some development of the body pressure measurement art, none of the devices disclosed are believed to be highly useful for locating the epidural space or the ligamentum-flavum. In fact, these devices are believed to be of essentially little or no use in trying to locate the epidural space or the ligamentum-flavum because, in locating the epidural space by locating the ligamentum-flavum, internal pressure measurement per se is not so important, but generation and measurement of an internal pressure gradient is of critical importance. To locate the ligamentum-flavum, the need is for generation, delivery and maintenance of gauge pressure of about eighty-four centimeters of water at the hypodermic needle tip. Research has established eighty-four centimeters of water as an ideal, expected equilibrium gauge pressure within the ligamentum-flavum, as contrasted to a zero or even negative gauge pressure within the epidural space.

SUMMARY OF THE INVENTION

This invention encompasses methods and apparatus for detecting probe penetration of human internal target tissue having predetermined internal pressure characteristics. This invention further encompasses a method and apparatus for detecting probe penetration of human epidural space having predetermined essentially negative gauge pressure characteristics.

Apparatus embodying aspects of the invention includes an elongated hollow probe, a valve having first and second orifices, with means for optionally connecting said orifices together, with the first orifice being connected to the hollow probe. A conduit is connected to the second orifice of the valve. Within the conduit there is moveable means for limiting maximum pressure, within the portion of the conduit connected to the hollow interior of the probe, to positive gauge pressure of ligamentum-flavum tissue proximate the epidural space, providing visible indication in said conduit interior portion when pressure between said movable means and said valve is equal to positive gauge pressure of the ligamentum-flavum.

The apparatus further includes means communicating with the conduit, at a position intermediate the moveable means and the valve means, all of which may be integrally connected, for increasing pressure within the conduit and the probe until the moveable means limits pressure within the conduit to positive gauge pressure of the ligamentum-flavum. The apparatus may further include biasing means for resisting movement of the moveable means in response to pressure build-up in the conduit due to the pressure increasing means increasing conduit internal pressure. The moveable means preferably has a passageway therethrough connecting a surface portion of the moveable means which receives pressure in the conduit with the surface portion of the moveable means which slideably contacts the conduit inner wall. The conduit wall has an orifice therethrough for communicating with the passageway at the slideably contacting surface portion of the moveable means when the moveable means has moved the slideably contacting surface portion thereof into communication therewith, in response to pressure build-up in the conduit due to operation of the pressure increasing means.

The apparatus may further encompass means for providing visible indication of when pressure in the first conduit interior portion, between the moveable means and the valve, is equal to the positive gauge pressure of the ligamentum-flavum tissue proximate said epidural space when a tip of the probe is in the ligamentum-flavum tissue and for providing visible indication of when pressure in the first conduit interior portion between the moveable means and the valve is equal to pressure in the epidural space when the tip of the probe is within the epidural space.

The invention further encompasses methods for detecting probe penetration of human epidural space having predetermined essentially negative gauge pressure and enlarging said epidural space in the neighborhood of the probe tip by anteriorly displacing the dura tissue bounding the epidural space away from the probe tip prior to injecting a therapeutically desired substance into the epidural space via the probe. Pressure in an essentially closed system defined by a probe hollow interior and a conduit communicating with the probe is increased until a moveable member, having a passageway therethrough connecting the portion of the conduit which communicates with the hollow probe interior, with an orfice formed in a moveable member lateral surface, reaches a position, in opposition to predetermined bias force applied to the moveable member, at which a passageway orifice formed in the lateral surface of the moveable member communicates with ambient air through the passageway in the wall of the conduit, thereby limiting internal pressure in the passageway to the essentially positive gauge pressure of the ligamentum-flavum.

After inserting a hollow probe towards the ligamentum-flavum having internal pressure substantially above atmospheric pressure, pressure is increased in an essentially closed system defined by the hollow probe interior and a conduit communicating with the probe by forcing gas into the system until a moveable member, including a passageway therethrough connecting the conduit with an orifice formed in a lateral surface of the moveable member which slideably contacts said conduit interior, moves within said conduit, in opposition to predetermined bias force which varies with movement of said movable member to a position at which said orifice in the lateral surface communicates with ambient air through a passageway in the wall of said conduit and at which said predetermined bias force corresponds to said predetermined internal pressure higher than gauge.

The probe travels through and pierces the ligamentum-flavum enroute to the epidural space, where the ligamentum-flavum tissue proximate the epidural space has a predetermined internal pressure higher than zero gauge pressure. The probe tip then extends through the ligamentum-flavum and into the epidural space which is then enlarged in the neighborhood of the probe tip by displacing the dura tissue bounding the epidural space anteriorly away from the probe tip—thus creating a dura tent. This is accomplished by increasing pressure in the epidural space through the balance of gas under pressure already within the closed system defined by the conduit and probe within the ligament-flavum, then releasing pressure into the epidural space and thereafter injecting a therapeutically desired substance into the epidural space through the hollow probe. Two types of pressure are applied, either singly or in combination, to enlarge the epidural space by anteriorly displacing the dura membrane boundary. One type of pressure exerted by the probe tip relates to the internal pressure of the closed system, which is directed along the longitudinal axis of the probe and outwardly from the tip. As the probe tip exits the ligamentum-flavum and enters the epidural space, there is a quick burst of pressure directed outwardly from the probe tip to a specific point within the space. The second type of pressure exerted by the probe tip relates to the pressure formed by continual and systematic operation of the probe as the probe traverses the ligamentum-flavum and then enters the epidural space. Thus, a constant pressure is applied over a large portion of the ligamentum-flavum and also a quick, localized burst of pressure is directed to a specific point within the epidural space—both of which result in the anterior displacement of the dura membrane boundary, creating a "dura tenting" phenomenon.

Further within the scope of the invention is apparatus that uses the internal characteristics of the ligamentum-flavum as a benchmark to locate the epidural space, through the generation and/or propagation and/or exertion and/or detection of either a positive pressure or a positive pressure gradient within and/or against such benchmark represented by the ligamentum-flavum.

A BRIEF DESCRIPTION OF THE DRAWINGS

FIG. 1 is a partially sectioned side elevation of apparatus embodying aspects of the invention.

FIG. 2 is a partially broken, partially sectioned enlarged view of a portion of apparatus shown in FIG. 1.

FIG. 3 is a side view of a stylet insertable into a portion of the apparatus shown in FIG. 1.

FIG. 4 is a partially broken side elevation of an alternate embodiment of the portion of apparatus illustrated in FIG. 2.

DESCRIPTION OF THE PREFERRED EMBODIMENTS AND BEST MODE FOR PRACTICING THE INVENTION

Referring to the drawings in general and to FIG. 1 in particular, apparatus for detecting probe penetration of epidural space and for enlarging said epidural space in the neighborhood of the probe, by displacing tissue bounding the epidural space away from the probe preparatory to injecting a therapeutically desired substance into the epidural space via the probe, is designated generally 10 and includes an axially elongated hollow needle-probe 12, a valve member, depicted schematically as 14, having first, second and third orifices designated 16, 18 and 20 respectively and including a rotatable central member, not shown, for optionally connecting any two or all three of orifices 16, 18, 20 together. Valve 14 is preferably a rotatable, conventional three-way stop cock valve, well-known in the art.

First orifice 16 is connected to and communicates with a hollow interior of needle-probe 12. Second orifice 18 is connected to and communicates with a hollow interior of a conduit 22 extending away from valve 14 as illustrated in FIG. 1. Third orifice 20 of valve 14 is connected to and communicates with means 24 for pumping medication into the hollow interior of needle-probe 12 through valve 14 via first and third orifices 16 and 20. Means 24 is preferably provided by a conventional thumb-powered syringe which may be removeably detached from valve member 14 and communicates therewith via a conduit 26. Connection means 28 between medication pumping means 24 and third conduit 26 is conventional.

Needle-probe 12 is preferably a standard blunt-tip seventeen gauge Tuey or Hausted puncture needle: however, other gauge needle sizes will also suffice. Probe 12 fits within a collar 30 disposed about an extended portion of third conduit 26. Valve 14 resides centrally with respect to third conduit 26. Third conduit 26 extends on either side of valve 14 to provide suitable orifices for communication of needle-probe 12 and medication pumping means 24 with valve 14. The first, second and third orifices of valve 14, namely orifices 16, 18 and 20 respectively, are within the housing for valve 14 defined generally by third conduit 26.

Collar 30 is rotatable to release needle-probe 12 from the extended portion of third conduit 26. Affixed to collar 30 is a pointer 32 positioned so that the tip of pointer 32 corresponds to the direction of the beveled tip 34 of the Tuey needle. Note that in FIG. 1 both pointer 32 and the bevel of tip 34 of the Tuey needle are in the plane of the paper.

The coupling provided by collar 30 between a base 36 of needle-probe 12 and the end 38 of third conduit 26 is conventional.

As illustrated in FIG. 1, needle-probe 12 and medication pumping means 24 preferably lie along an axis of alignment with third conduit 26 and valve member 14. Preferably, medication pumping means 24 can be disconnected from conduit 26 at juncture 28 and an appropriate stylet, such as shown in FIG. 3, may be inserted at juncture 28 through conduit 26 and through the interior of hollow needle-probe 12 to extend to needle tip 34.

Conduit 22 preferably extends transversely away from the axis of conduit 26, as illustrated in FIG. 1. A second conduit 40 communicates with first conduit 22, preferably at a position slightly removed from juncture of first conduit 22 with second orifice 18. Second conduit 40 preferably extends away from first conduit 22 at an angle of about 45° and, accordingly, second conduit 40 preferably makes an angle of about 45° with the axis of alignment of third conduit 26, probe 12, medication pumping means 24 and the like. At an end of second conduit 40 remote from the point of communication between first conduit 22 and second conduit 40 is a hand squeezable bulb 42 providing means for increasing pressure within conduits 22 and 40, and also within hollow probe 12 when valve member 14 is positioned for communication between the hollow interior of needle-probe 12 and the interior of conduit 22.

Slideably resident within conduit 22 is a moveable piston 44 including a passageway 46 therethrough. This structure is best shown in FIG. 2. A resilient coil spring 52 applies bias to moveable piston 44 in opposition to internal pressure within conduit 22, acting against piston 44. Spring 52 may reside within conduit 22, between moveable piston 44 and a cap member 54 which closes the end of conduit 22 remote from valve 14.

Referring to FIG. 2, conduit 22 includes an orifice 56 formed in the side wall thereof, providing communication between the hollow interior 58 of conduit 22 and ambient atmosphere. Moveable piston 44 has a bottom surface 60 receiving internal pressure within conduit 22. Pressure within conduit 22 acting against the area of piston bottom surface 60 produces a force directed upwardly in FIG. 2, tending to move piston 44 upwardly within conduit 22 against bias provided by spring 52.

Piston 44 has a lateral side surface 62 slideably contacting interior surface 64 of conduit 22. Passageway 46 through piston 44 terminates at respective orifices 66, 68 formed respectively in bottom surface 60 and lateral surface 62 of piston 44. While piston 44 may move reciprocably within conduit 22 in the direction indicated by arrow A in FIG. 2, piston 44 is precluded from rotating within conduit 22 about the axis thereof. Any suitable means may be used to preclude such rotation. For example, piston 44 and the interior of conduit 22 may be configured with a square cross-section but may be provided with a track or runner axially extending within conduit 22 to prevent rotation of piston 44. In the embodiment illustrated in FIGS. 1 and 2, the rectangular cross-section of rod 50 fitting slideably within a corresponding rectangular clearance passageway of cap 54 prevents such rotation because rod 50 is affixed to piston 44. Lateral side surface 62 and conduit internal surface 64 mate closely so liquid or air under pressure cannot escape from the conduit interior between the piston and the conduit wall.

Piston 44 is not permitted to rotate within conduit 22, in order to assure that as piston 44 rises to the position illustrated in FIG. 2, orifice 68 in lateral surface 62 of piston 44 communicates with orifice 56 in the sidewall of conduit 22. At the position shown in FIG. 2, pressure within conduit 22 is reduced to atmospheric as gas or liquid within conduit 22 escapes to atmospheric via passageway 46.

Spring 52 is selected to have a spring constant and is positioned so that piston 44 will reach the position at which orifice 68 communicates with orifice 56 when pressure within conduit 22 equals a preselected pressure corresponding to internal pressure of a selected human organ. Dimensions of the apparatus are correspondingly selected according to the desired preselected pressure. For example, if the apparatus is to be used to detect penetration of the ligamentum-flavum by the needle-probe tip, spring 52 and the position of orifice 56 are selected so that the preselected pressure, at which passageway 46 communicates with orifice 56, is eighty-four centimeters of water.

When the predetermined pressure is reached within conduit 22, piston pressure is relieved via escape of gas through passageway 46 and orifice 68. Once the pressure is slightly relieved, bias applied by spring 52 forces piston 44 downwardly as viewed in FIG. 2, thereby interrupting communication between passageway 46 and orifice 68, once again sealing the interior of conduit 22 against escape of pressurized liquid or gas therefrom. In operation, when the physician advances probe 12 into the epidural space from the ligamentum-flavum, piston 44 slides downwardly in response to spring 52 bias force, thereby sealing conduit 22 and permitting pressure in the system to equalize.

Referring once again to FIG. 1, conduit 40 and hand squeezable bulb 42 are preferably coplanar with probe 12, valve 14 and medication pumping means 24, as illustrated in FIG. 1. The angular configuration of the portion of conduit 40 communicating with conduit 22, coupled with the bend in conduit 40 (so that the portion of conduit 40 with which bulb 42 communicates is essentially parallel with the axis of alignment of probe 12, valve 14 and medication pumping means 24) permits comfortable hand positioning by the operator of the apparatus.

Typically, a physician may grasp the apparatus by gripping conduit 26 with the first two fingers of his left hand and applying his thumb to piston 25 to inject a therapeutically desired pharmaceutical substance into the patient. With the apparatus thus held by his left hand, the physician can use his right hand to pump squeeze bulb 42 thereby to increase pressure within conduit 22, and within the hollow interior of probe 12 if valve 14 is positioned for communication therebetween.

In one preferred embodiment of the invention, hand squeezable bulb 42 supplies a constant volume of three cubic centimeters of air each time the bulb is substantially completely squeezed. The bulb 42 preferably includes a dorsal opening conveniently positioned to be covered by the operator's thumb, with the opening indicated as 43 in FIG. 1. Opening 43, when uncovered by the operator's thumb, permits rapid refill of hand squeezable bulb 42.

The apparatus may be used in practicing methods of the invention for determining location and penetration by probe 12 of the ligamentum-flavum, detecting probe 12 penetration into the epidural space and enlarging the epidural space in the neighborhood of the tip of probe 12 by anteriorly displacing tissue bounding the epidural space away from the tip of probe 12. To locate the ligamentum-flavum in the body, the physician, utilizing the apparatus disclosed in FIG. 1, selects a desired spot between two vertebrae, at which the ligamentum-flavum is to be located. Gripping the apparatus of FIG. 1 with one hand, the physician inserts needle-probe 12 slowly into the body. As the needle is advanced, the physician rapidly squeezes and refills bulb 42, thereby sending forth in rapid succession constant volume bursts of air, preferably three cubic centimeters each, that effectively bombard the tissues encountered by needle tip 34 as it approaches the ligamentum-flavum. While doing this the physician watches scale 48, as piston 44 moves upwardly within conduit 22 and pressure indicating indicia rod 50 extending from piston 44 rises unitarily with piston 44. The physician continues to squeeze bulb 42, thereby continuing to inject air into the system defined by the interior of conduit 22 and the hollow interior of needle-probe 12. Valve 14 is positioned so that conduit 22 communicates with hollow interior of needle-probe 12 and medication pumping means 24 is isolated from the remainder of the system.

As pressure within conduit 22 rises and approaches eighty-four centimeters of water, indicating intersection of the tip 34 of the hollow needle-like probe 12 with the boundary of the ligamentum-flavum, orifice 68 in piston 44 approaches orifice 56 in the side wall of conduit 22. Upon tip 34 penetrating the core of the ligamentum-flavum, the system closes, due to the internal pressure characteristics of the ligamentum-flavum. As the pressure reaches eighty-four centimeters of water, piston 44 rises to a point where orifices 56 and 68 communicate, thereby allowing partial venting of increased internal pressure which prevents internal pressure within the system from exceeding eighty-four centimeters of water. In order for piston 44 to rise, the physician squeezes bulb 42. At the time when orifices 56 and 68 communicate, bulb 42 collapses as excess internal pressure is vented. Resultant venting and relief of internal pressure permits spring 52 to move piston 44 slightly downwardly within conduit 22, thereby breaking communication between orifice 68 and 56.

When piston 44 moves slightly downwardly within conduit 22, breaking connection between orifices 56 and 68 and re-establishing the "essentially closed" character of the system, the attending physician should maintain the bulb in its already collapsed state which the bulb assumed when the system vented to the atmosphere due to the brief communication between orifices 56 and 68. The attending physician accomplishes this by maintaining his thumb in position covering opening 43 of bulb 42. This collapsed state of bulb 42 reduces the internal volume of the re-established essentially closed system, making piston 44 even more responsive to pressure encountered by tip 34 of needle-like probe 12 and independent of other external influences. Note that at this point the attending physician relies only on the visibly signaled pressure as an indication of the location of tip 34 of needle-like probe 12. He does not rely on any tactile sensation.

Due to the re-established "essentially closed" nature of the system, pressure within the system will be maintained at eighty-four centimeters of water, which signifies that needle tip 34 is within the ligamentum-flavum; positive pressure of eighty-four centimeters of water indicates the interior of the ligamentum-flavum. The hand squeezable bulb 42 remains compressed, yet pressure within the system, as indicated by indicia 50, remains at eighty-four centimeters of water due to its balance with the internal pressure of the ligamentum-flavum as propagated via probe 12 and conduit 22 to the lower surface of piston 44.

Once the ligamentum-flavum has been sensed and located, advancement of needle probe 12 a few fractions of a centimeter causes tip 34 to penetrate the epidural space. Such penetration is indicated by a sudden downward plunge of calibrated indicia bearing rod 50, from eighty-four centimeters of water to zero centimeters of water, which is indicative of the essentially zero pressure within the epidural space being propagated into the system.

Once this movement of calibrated indicia bearing rod 50 has confirmed entry of needle tip 34 into the epidural space, the epidural space is ready to be injected within appropriate medication or anesthetic. However, before this is done, the needle tip should be manually rotated by turning collar 30 to a position at which pointer 32, and hence bevel tip 34 of needlepoint 12, points either directly downwards or upwards, assuming the patient is lying on his or her side, in a direction transverse to the axis of the patient's spinal cord. This insures proper spread of the injectate, either downwards or upwards, within the epidural space, thereby effectively limiting the injectate to a given location along the length of the spinal column. If this is not done, parallel spread or flow of the injectate may result, with inferior or undesired therapeutic results.

FIG. 4 illustrates another embodiment of the apparatus in which piston 44' has a spherical shape with bias member 52' secured to the upper extremity of conduit 22'. Piston 44' may be a metal or plastic ball assembly, with the size of piston 44' being selected so that a liquid and gas-tight seal is achieved between piston 44' and the interior wall of second conduit 22'. As illustrated, there may be a support member 100' in the second conduit 22' for supporting piston 44' and limiting downward travel thereof. The support member is apertured, as shown by dotted lines, to provide fluid communication between the lower section of piston 44' and the portion of conduit 22' most proximate the valve which has not been illustrated in FIG. 4.

In the embodiment illustrated in FIG. 4, pressure indicating indicia appear on the side wall of second conduit 22' since the piston rod has been eliminated. Preferably the wall of conduit 22' is transparent so that the operator of the apparatus can observe movement of piston 44' upwardly and downwardly within conduit 22' and thereby determine the internal pressure within the system based on where piston 44' is along the scale of pressure indicating indicia. Functional equivalents of other parts in FIG. 4 corresponding to those in FIG. 2 have not been numbered in FIG. 4, to assure drawing clarity. However, the pressure indicating indicia operate in the manner of that attached to the piston rod.

In yet another embodiment of apparatus of the invention, passageway 46 is omitted from piston 44 and orifice 56 is omitted from the side wall of conduit 22. When the apparatus of FIG. 1 is so-modified, the necessary pressure gradient for detecting penetration of the ligamentum-flavum be needle tip 34 may still be determined by observing pressure via movement of rod 50. However, independent maintenance of system internal pressure equal to internal pressure of the ligamentum-flavum cannot be verified using this modified embodiment of the apparatus.

I claim the following:

1. A method for detecting probe penetration of human epidural space having predetermined essentially negative gauge pressure relative to atmosphere pressure and enlarging said epidural space in the neighborhood of said probe by displacing tissue bounding said epidural space away from said probe, prior to injecting a therapeutically desired substance into said epidural space via said probe, comprising:
   (a) inserting a hollow probe into the human body towards said epidural space and into ligamentum-flavum tissue having internal pressure substantially above atmosphere, proximate said epidural space;
   (b) increasing pressure in an essentially closed system within the ligamentum-flavum, defined by said probe hollow interior and a conduit communicating with said probe by forcing gas into said system until a moveable member, including a passageway therethrough connecting said conduit with an orifice formed in a lateral surface of the moveable member which slidably contacts said conduit interior, moves within said conduit, in opposition to predetermined bias force which varies with movement of said moveable member, to a position at which said orifice found in said lateral surface communicates with ambient air through a passageway in the wall of said conduit and at which said predetermined bias force corresponds to said predetermined internal pressure higher than gauge:
   (c) moving said probe further through said tissue generally proximate said epidural space and having predetermined internal pressure higher than zero gauge pressure, towards said epidural space so that the probe tip moves from said tissue to penetrate said epidural space with said probe tip;
   (d) enlarging said epidural space in the neighborhood of the probe tip by anteriorly displacing dura tissue bounding said epidural space away from said probe tip by increasing pressure in the ligamentum-flavum and subsequently releasing gas under pressure within said probe into said epidural space; and
   (e) injecting said therapeutically desired substance into said enlarged epidural space through said hollow probe.

2. The method of claim 1 wherein increasing the depth of insertion of said probe and injecting gas into an essentially closed system defined by said probe hollow interior and said conduit between said probe and said moveable member are performed simultaneously.

3. The method of claim 2 further comprising applying bias to said moveable member in opposition to pressure acting against said moveable member in said conduit.

4. The method of claim 3 wherein injecting gas in performed by repeatedly squeezing a constant volume hand bulb.

5. The method of claim 4 wherein said gas is air.

6. The method of claim 4 wherein said gas is inert.

* * * * *